(12) United States Patent
Schwarz et al.

(10) Patent No.: US 7,741,629 B2
(45) Date of Patent: Jun. 22, 2010

(54) APPARATUS FOR ANALYSING SURFACE PROPERTIES WITH INDIRECT ILLUMINATION

(75) Inventors: Peter Schwarz, Koenigsdorf (DE); Uwe Sperling, Geretsried (DE)

(73) Assignee: BYK-Gardner GmbH (DE)

( * ) Notice: Subject to any disclaimer, the term of this patent is extended or adjusted under 35 U.S.C. 154(b) by 31 days.

(21) Appl. No.: 11/859,673

(22) Filed: Sep. 21, 2007

(65) Prior Publication Data

US 2008/0073603 A1   Mar. 27, 2008

(30) Foreign Application Priority Data

Sep. 22, 2006 (DE) .................. 10 2006 045 285

(51) Int. Cl.
*G01N 21/86* (2006.01)
*G01N 21/00* (2006.01)
*G01N 21/47* (2006.01)

(52) U.S. Cl. .......................... 250/559.01; 356/237.2; 356/446

(58) Field of Classification Search ............ 250/559.01, 250/559.16–559.19, 239, 216; 356/335–338, 356/342–343, 445–446, 220–221, 237.2, 356/237.3, 237.4, 237.5, 600–601; 362/545
See application file for complete search history.

(56) References Cited

U.S. PATENT DOCUMENTS

| 4,113,386 | A | * | 9/1978 | Lepper, Jr. ............... 356/338 |
| 5,111,037 | A | * | 5/1992 | Boderie et al. ........... 250/216 |
| 6,738,165 | B2 | * | 5/2004 | Sawada .................... 358/475 |
| 7,006,229 | B2 | * | 2/2006 | Sperling et al. .......... 356/445 |
| 2001/0030744 | A1 | * | 10/2001 | Chang ..................... 356/237.3 |
| 2006/0109473 | A1 | * | 5/2006 | Doak et al. .............. 356/445 |

\* cited by examiner

*Primary Examiner*—Georgia Y Epps
*Assistant Examiner*—Don Williams
(74) *Attorney, Agent, or Firm*—Hayes Soloway P.C.

(57) ABSTRACT

An apparatus (1) for analysing surface properties, comprising a first radiation device (4) which emits radiation directly onto a surface (9) to be analyzed, a first illumination device (6, 7) for indirectly illuminating the surface (9) to be analyzed, a first radiation detector device (8) which receives at least part of the radiation thrown back from the surface (9) to be analyzed and outputs at least one signal which is characteristic of this part of the radiation. According to the invention, a radiation scattering device (10, 11) is provided which is at least partially illuminated by the first illumination device (6, 7) and which transmits scattered radiation onto the surface (9) to be analyzed.

15 Claims, 3 Drawing Sheets

APPARATUS FOR ANALYSING SURFACE PROPERTIES WITH INDIRECT ILLUMINATION

FIELD OF THE INVENTION

The present invention relates to an apparatus and a method for determining surface properties. The invention will be described with reference to surfaces of motor vehicles. However, it is pointed out that the invention can also be used on other surfaces, for example the coatings of furniture, of floor coverings and the like.

BACKGROUND OF THE INVENTION

The optical impression of objects or of the surfaces thereof, particularly surfaces on motor vehicles, is greatly determined by the surface properties thereof. However, since the human eye is suitable only to a limited extent for the objective determination of surface properties, there is a need for aids and apparatuses for the qualitative and quantitative determination of surface properties.

Surface properties such as, for example, gloss, orange peel, colour, macrostructure or microstructure, image sharpness, haze, surface structure and/or surface topography and the like are determined.

The prior art discloses apparatuses in which a radiation device emits radiation onto a surface to be analysed and the radiation reflected and/or scattered by this surface is received by a detector and evaluated. The optical appearance of paintwork changes not only as a function of the type of light but also as a function of the type of illumination which is irradiated onto the surface. For instance, a paint has a different appearance under direct sunlight than in diffuse light (for example when the sky is cloudy).

The object of the present invention is therefore to assess paintwork or surfaces also as a function of the light impinging thereon. In particular, it should be possible to assess the surface properties under scattered light and diffuse light.

According to the invention, this is achieved by an apparatus and by a method. The apparatus according to the invention for analysing surface properties comprises a first illumination device for indirectly illuminating a surface to be analyzed. Also provided is a first radiation detector device which receives at least part of the radiation thrown back from (i.e. in particular reflected and/or scattered by) the surface to be analysed and outputs at least one signal which is characteristic of this part of the radiation. According to the invention, a radiation scattering device is provided which is at least partially illuminated by the first illumination device and which transmits scattered radiation onto the surface to be analysed.

Preferably, a first radiation device is also provided which emits radiation directly onto the surface to be analysed. Here, indirect illumination is understood to mean that the illumination device does not illuminate the surface directly, but rather illuminates the aforementioned radiation scattering device and then the light scattered by this radiation scattering device passes onto the surface. In particular, the radiation scattering device is a radiation scattering device which is non-transmitting for the light emitted by the illumination device. In other words, no direct or straight beam path runs from the illumination device to the surface to be analysed.

By using the radiation scattering device, it is possible to simulate the illumination of a surface with diffuse light.

The radiation is preferably light in a visible wavelength range, and also the illumination device preferably emits light in visible wavelength ranges.

In one preferred embodiment, the radiation scattering device is essentially completely surrounded by a radiation-absorbent region. This prevents the radiation scattering device from being inadvertently hit also by rays from the radiation device, and in this way prevents any mixing between the indirect and the direct illumination of the surface. The radiation scattering device according to the invention is also intended in particular to bring about the situation whereby the indirect illumination and the direct irradiation of the surface are completely separate from one another and for example the direct irradiation does not also have indirect components.

In one preferred embodiment, the radiation scattering device is arranged outside a plane which is arranged through the radiation direction in which the rays are transmitted from the first radiation device to the surface, and a second radiation direction which extends between the surface and the radiation detector device. This plane is in particular also a centre plane of the apparatus. By arranging the radiation scattering device outside this plane, it is possible to prevent the radiation scattering device from being hit by the radiation device, and in this way undesirable mixing of direct and indirect illumination can be prevented.

In a further advantageous embodiment, a second radiation scattering device is provided and the first and the second radiation scattering device are arranged essentially symmetrically with respect to a centre plane of the apparatus. This centre plane is once again in particular the aforementioned plane of the apparatus. By virtue of this symmetrical arrangement of the two radiation scattering devices with respect to this plane, it is possible to simulate in a particularly advantageous manner scattered light coming from all sides, as occurs for example in the case of a very cloudy sky.

In a further advantageous embodiment, the first radiation scattering device and the first illumination device, which illuminates the first radiation scattering device, are arranged on different sides with respect to the centre plane. This means that the radiation scattering device is illuminated as it were from the opposite side of the plane. In another embodiment, it would also be possible that the illumination device and the radiation scattering device are arranged on the same side of the plane, and the illumination device for example is provided with a reflector in order to illuminate the radiation scattering device.

In a further advantageous embodiment, two radiation scattering devices are provided which are arranged symmetrically with respect to the centre plane, and also two illumination devices which respectively illuminate the radiation scattering devices located opposite them with respect to the centre plane. In this way, it is possible to simulate in a particularly efficient manner diffuse radiation coming from all sides.

In a further preferred embodiment, at least one illumination device is arranged within a radiation scattering device. In other words, the radiation scattering device here is an area within which the illumination device is provided. The illumination device is preferably provided essentially centrally within the radiation scattering device. The beam path between the radiation scattering device and the respective opposite illumination device is preferably also essentially perpendicular to the abovementioned centre plane. The illumination device is particularly preferably an illumination device which contains a light-emitting diode (LED). This is particularly preferably a white light-emitting diode, but it would also be possible to use light-emitting diodes with several colour components, for example red, green and blue light-emitting diodes, in order in this way to produce white light. Ideally, the spectral distribution of the white LED corresponds to a standard type of light, e.g. D65, and the detector corresponds to a v($\lambda$) distribution (eye sensitivity function).

Since both criteria cannot be achieved exactly, the product $P(\lambda)$ of the type of light used and the sensitivity of the detector is adapted to the target product of the aforementioned type of light D65 and the aforementioned target $v(\lambda)$ distribution.

In one preferred embodiment, the or at least one radiation detector device allows local resolution of the radiation impinging thereon. In this way, a locally resolved image can be output. In this case, the radiation detector device may in particular have a CCD chip or the like which outputs a locally resolved image of the radiation impinging thereon.

In a further advantageous embodiment, the radiation scattering device has circular or elliptical profile. In addition, the profile is preferably spherical, i.e. the radiation scattering device has an outward curvature with respect to the centre plan. It is also possible for circular and elliptical profiles to be combined.

Preferably, the radiation scattering device has a reflective coating, wherein the degree of reflection of this coating is particularly preferably greater than 0.9 for light in a wavelength range of 250-1500 nm and particularly preferably greater than 0.97 for light in the visible range.

The apparatus preferably has a housing with an opening, through which the surface can be illuminated. With the exception of this opening, however, this housing is closed in order to prevent light from outside impinging on the surface and falsifying the measurement.

The radiation scattering device is preferably arranged on or in a side wall of this housing. With particular preference, the two radiation scattering devices are arranged in or on opposite side walls of the housing.

In a further preferred embodiment, at least one radiation scattering device is arranged at a distance from the surface in a direction perpendicular to the surface. This means in particular that the radiation scattering device does not directly adjoin the opening but rather is at a distance therefrom. With particular preference, a light-absorbent intermediate region is provided between the radiation scattering device and the opening. This light-absorbent intermediate region serves in particular to prevent or absorb other scattered light. Particularly preferably, a region coated with photoresist is provided as the absorbent intermediate region.

In a further preferred embodiment, a third radiation scattering device or a radiation scattering body is provided which runs at least in some sections in the centre plane. Preferably, this is a region which is thus arranged at least partially above the surface to be analysed and preferably is arranged essentially vertically above the latter. This region may also be partially illuminated by the illumination device, and in this way an even better match to natural scattered light can be achieved.

In a further preferred embodiment, the apparatus has at least one radiation-absorbent cover device, by means of which at least one radiation scattering device can be at least partially covered. This cover device means that the radiation scattering device does not falsify the measurement with direct irradiation of the surface.

In a further preferred embodiment, a plurality of radiation devices are provided which directly irradiate the surface at different angles. In addition, a plurality of radiation detector devices may also be provided.

In a further preferred embodiment, a movement device is provided in order to move the apparatus with respect to the surface to be analysed. In addition, a distance measurement device may also be provided which determines the length of the path traveled with respect to the apparatus. These embodiments mean that the images recorded by the radiation detector device can be output as a function of a location on the surface.

The present invention also relates to a method for analysing surface properties, wherein a surface to be analysed is indirectly illuminated by a first illumination device and the radiation thrown back from the surface is at least partially received by a radiation detector device and a signal is output which is characteristic of the radiation received by the radiation detector device. According to the invention, a radiation scattering device is provided which is at least partially illuminated by the first illumination device and which transmits scattered radiation onto the surface to be analysed.

Furthermore, the surface to be analysed is advantageously irradiated directly by a radiation device and also the light thrown back from the surface is received by the radiation detector device and analysed. With particular preference, the illumination by the illumination device and the direct irradiation by the radiation device take place in a temporally offset manner.

The present invention therefore also relates to the use of the apparatus according to the invention for discovering particular colour values, in particular from a table of colour values. This use is relevant in particular in the motor vehicle repair sector. Furthermore, the invention can be used to produce a specific target colour by means of a specially adapted colour recipe system. Furthermore, measured values output by the apparatus according to the invention can be used for simulation purposes, in particular but not exclusively on the screen.

BRIEF DESCRIPTION OF THE DRAWINGS

Further embodiments and advantages will emerge from the appended drawings, in which.

DETAILED DESCRIPTION OF THE INVENTION

Figure 1:
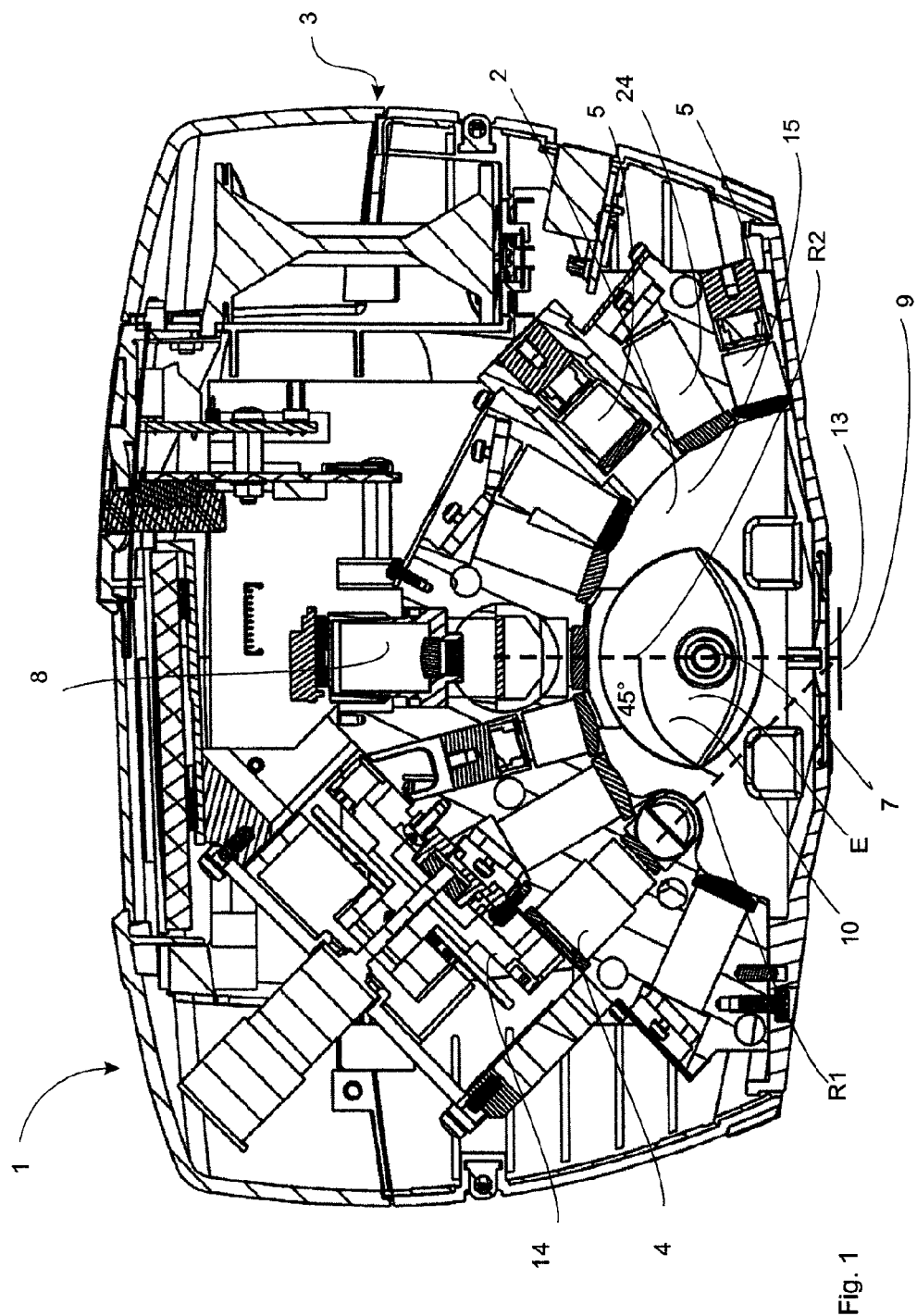
FIG. 1 shows a side view of an apparatus according to the invention.

FIG. 1 shows a side view of an apparatus 1 according to the invention for analysing surface properties. This apparatus comprises a first radiation device 4 which emits radiation along the direction R1 onto a surface 9 to be analysed. For this purpose, the housing 3 of the apparatus has an opening 13, through which the radiation can pass and impinge on the surface 9. This opening 13 is essentially the only opening of the housing. In this way, it is possible to prevent disruptive external light from passing into the observation area 2 of the apparatus. Reference 8 denotes a radiation detector device which serves to receive the light that is thrown back from the surface 9, i.e. in particular the light that is reflected and/or scattered by the surface 9. The first radiation device 4 is arranged here at an angle of 45° with respect to the centre vertical line R2. Reference R2 denotes the direction which extends between the surface 9 and the radiation detector device 8. Together, these two directions R1 and R2 form the plane E, which here coincides with the plane of the figure.

Reference 15 denotes a carrier (which will be described in detail in FIGS. 3a and 3b), on which a radiation scattering device 10 is arranged.

References 5 denote further radiation devices which in each case emit radiation onto the surface at different angles with respect to the direction R2. Reference 24 denotes further radiation detector devices, in particular for measuring the surface under direct illumination and/or irradiation.

The plane of the carrier 15 is likewise offset laterally (towards the front or rear) with respect to the centre plane E. The radiation scattering device 15 has a spherical profile which will be explained in detail below and which is curved outwards with respect to the carrier 15. An illumination device 7 is arranged within the radiation scattering device. This illumination device 7 illuminates a radiation scattering device (not shown) which is located opposite it in this case. Arranged within the opposite radiation scattering device (not shown) is a further illumination device which in turn illuminates the radiation scattering device 10 shown in FIG. 1. The radiation scattering device 10, which is provided with a highly reflective (and therefore greatly scattering) coating, is thus illuminated by the opposite illumination device (not shown) and in turn illuminates the surface 9, so that the surface 9 is illuminated indirectly by the illumination devices 7.

Figure 2:
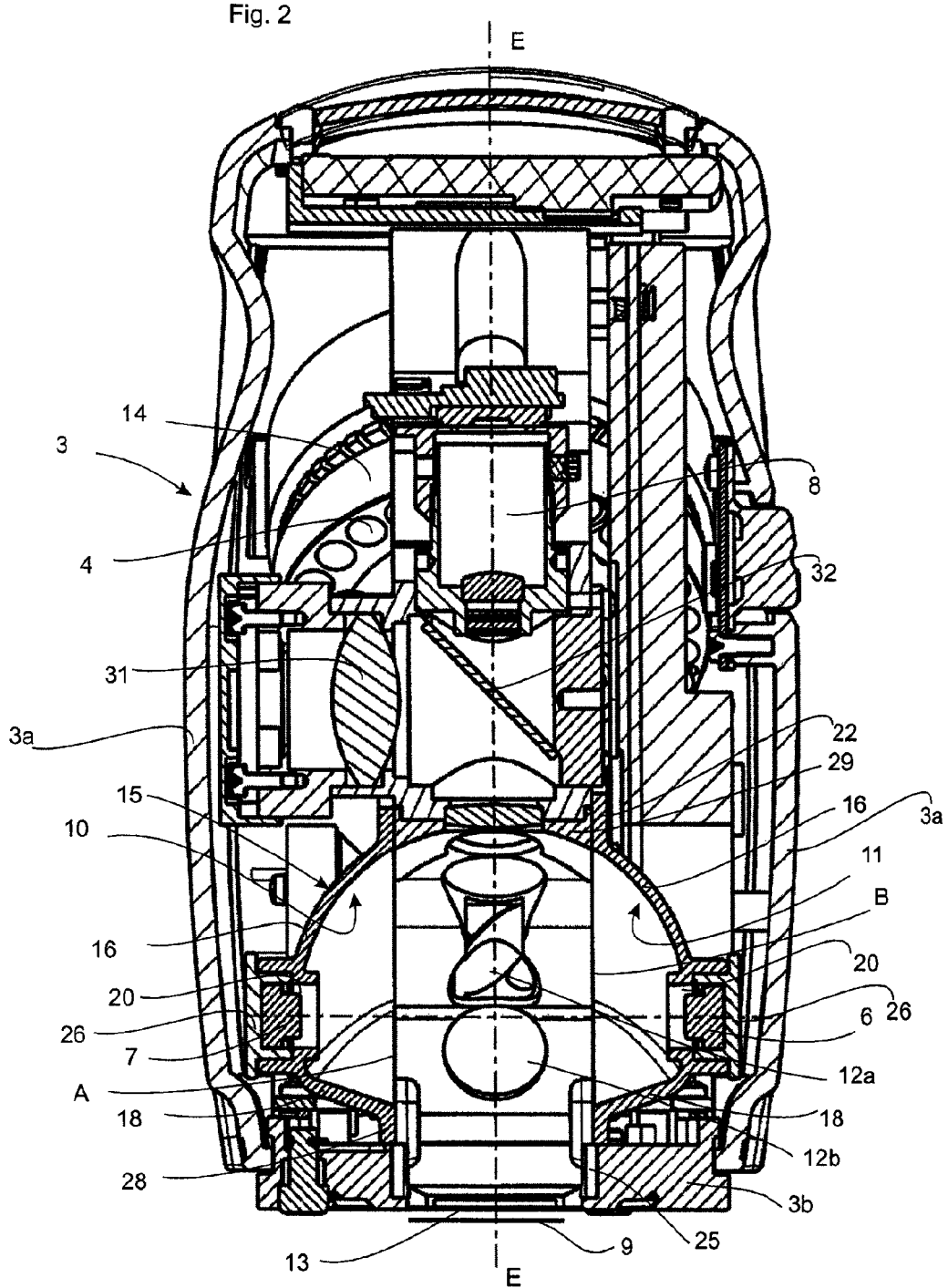
FIG. 2 shows a section through the apparatus of FIG. 1.

FIG. 2 shows a section rotated by 90° through the apparatus shown in FIG. 1. Here, reference 4 denotes a radiation device, wherein in this case for example a plurality of LEDs of different colours are arranged on a carrier wheel 14. References 12a, 12b denote further lens systems which are provided for further radiation devices and radiation detector devices of the apparatus according to the invention. Via a beam splitter 32 and a lens 31, part of the light radiated onto the radiation detector device can be coupled onto a further detector device for intensity measurement purposes and in this way an integral colour measurement is also carried out.

Reference 3b denotes a housing base, on which the carrier 15 is arranged by means of fixing elements 25. The radiation scattering device 10 has an upper region 16 and a lower region 18. The two regions are coated on the inside, i.e. towards the plane E, with a highly reflective coating. The lower region 18 is adjoined in the downward direction by an absorbent transition region 28.

Due to the special design of the radiation scattering device 10, 11, it is possible to prevent light from the radiation device 4 from also impinging on the radiation scattering device 10 and thus falsifying measurements under direct illumination. Reference 20 denotes openings in the radiation scattering devices 10, 11, wherein illumination devices 6, 7 in the form of so-called power LEDs are arranged in each of these openings. These power LEDs are mounted on carriers 26. This carrier at the same time closes off the opening 20 against light from the outside.

Reference 3a denotes side walls of the housing 3, which likewise essentially close off the interior against light.

Reference 29 in FIG. 2 denotes a radiation scattering body which is arranged within the two lines A and B in FIG. 2. This scattering body 29 also intersects the centre plane E and is likewise at least partially illuminated by the illumination devices 6 and 7, but not by the radiation device 4. Due to the interaction of the radiation scattering devices 10, 11 and of the radiation scattering body 29, particularly advantageous illumination of the opening 13 and thus of the surface 9 is achieved and hence diffuse light is simulated in a particularly advantageous manner.

Figure 3A:
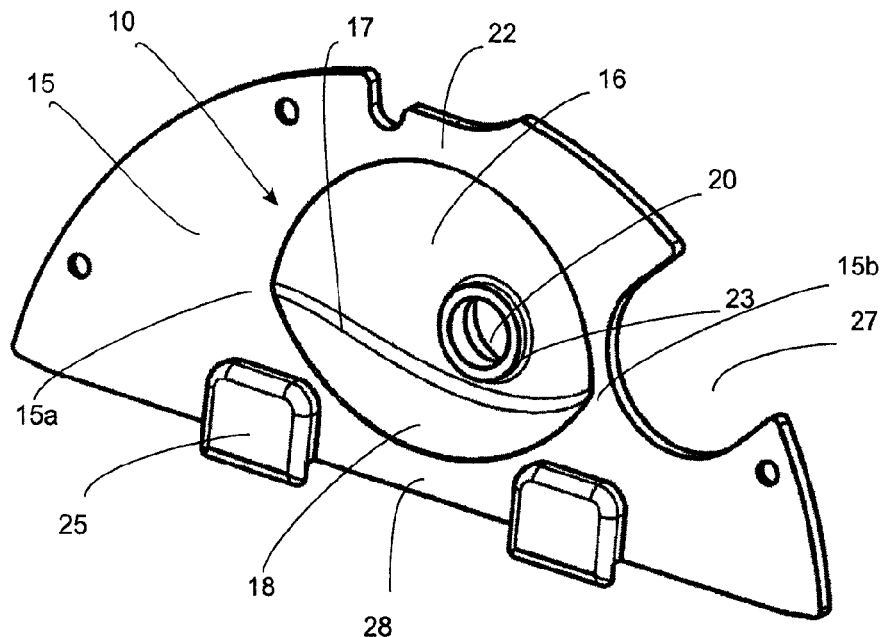
FIG. 3a shows a front view of a radiation scattering device.

FIG. 3a shows a front view of a carrier 15 according to the invention with a radiation scattering device 10. It can be seen that the upper region 16 of the radiation scattering device 10 has an essentially semi-circular cross section. The lower region 18 of the radiation scattering device has a semi-elliptical cross section. The upper region 16 and the lower region 18 merge into one another via an edge 17. The opening 20 is delimited by a peripheral edge 23 which holds the illumination device (not shown). An absorbent region 28 is provided below the radiation scattering device 10 or the lower region 18 thereof. Reference 27 denotes a cutout which serves to receive optical components of the radiation device 4 (cf. FIG. 1).

Figure 3B:
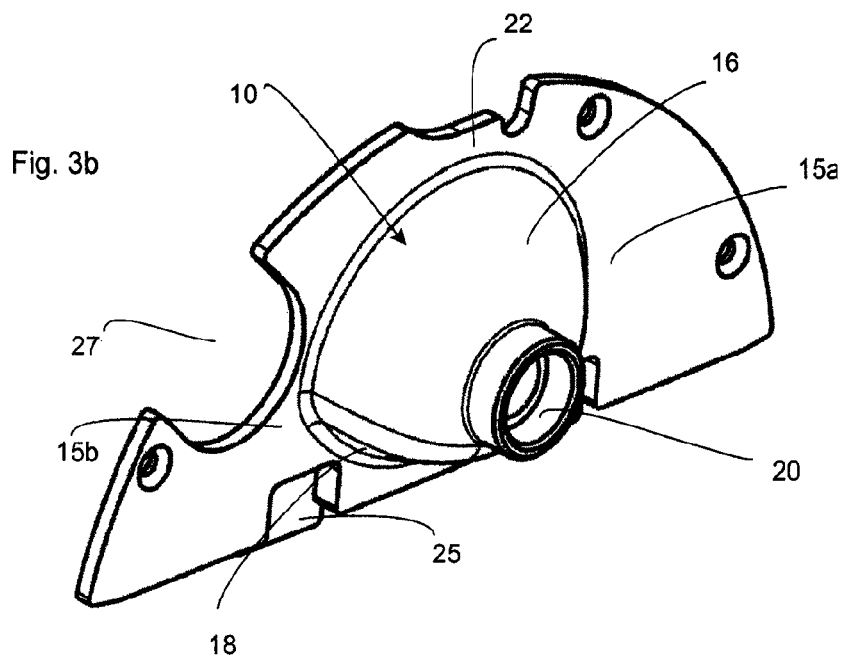
FIG. 3b shows a rear view of a radiation scattering device according to the invention.

FIG. 3b shows a rear view of the carrier 15 shown in FIG. 3a. It can be seen that the upper region 16 of the radiation scattering device 10 is curved spherically outwards. The lower region also has an outward spherical curvature (not shown). Here, however, the opening 20 is not arranged centrally within the radiation scattering device but rather the lower region 18 has a smaller surface area than the upper region 16 of the radiation scattering device. The special geometric shape, i.e. the two spherical configurations of the upper region 16 and of the lower region 18, give rise to a particularly advantageous scattered radiation if the entire region is illuminated by the respective LED located opposite. The regions 22 shown above the upper region 16 in FIGS. 3a and 3b are also radiation-absorbent. This also applies in respect of the other surfaces 15a and 15b which laterally delimit the radiation device 10. As can be seen from FIGS. 3a and 3b, the regions and surfaces 15a, 15b, 28 and 22 are arranged in one plane. The entire carrier 15 with the exception of the radiation scattering device 10 is thus designed to be absorbent.

If the entire carrier were to be provided with a highly reflective coating, the efficiency of the diffuse illumination would be improved but disruptive scattered light would be produced which passes directly from the scattering device onto the detector. For the same reason, the radiation scattering device is not designed as a hemisphere overall, but rather is composed of the hemispheres and semi-ellipses shown in FIGS. 3a and 3b.

In general, the shape of the radiation scattering device will be selected in such a way that no scattered light can pass directly from the radiation scattering device into the radiation detector device(s). The outwardly curved shape of the radiation scattering device also serves for this purpose. In series of complicated tests, the shape of the radiation scattering device shown here proved to be particularly suitable both for the requirement of the most uniform possible illumination of the surface and for the requirement of avoiding direct scattered light which passes from the radiation scattering device onto the radiation detector device.

All the features disclosed in the application documents are claimed as essential to the invention in so far as they are novel individually or in combination with respect to the prior art.

LIST OF REFERENCES 1 apparatus for analysing surfaces
2 observation area
3 housing
3a side walls
3b housing base
4 first radiation device
5 further radiation devices
6 illumination device
7 illumination device
8 radiation detector device
9 surface
10,11 radiation scattering device
12a, 12b lens systems
13 opening
14 carrier wheel
15 carrier 15a, 15b surfaces of the carrier 15
16 upper region of the radiation scattering device
17 edge
18 lower region of the radiation scattering device
20 opening in the radiation scattering device
22 absorbent region
23 peripheral edge
24 further radiation detector devices
25 fixing elements
26 carrier
27 cutout
28 absorbent transition region
29 radiation scattering body
31 lens
32 beam splitter
A line
B line
E centre plane
R1 direction
R2 direction

The invention claimed is:

1. An apparatus for analysing surface properties, comprising a first radiation device which emits radiation directly onto a surface to be analysed, a first illumination device for indirectly illuminating the surface to be analyzed, at least one first radiation detector device which receives at least part of the radiation thrown back from the surface to be analysed and outputs at least one signal which is characteristic of this part of the radiation, wherein a radiation scattering device is provided which is at least partially illuminated by the first illumination device and which scatters radiation, and transmits the scattered radiation onto the surface to be analyzed, wherein the radiation scattering device is arranged outside a plane (E) which is arranged through a first radiation direction (R1), in which rays are transmitted from the first radiation device to the surface, and a second radiation direction (R2) which extends between the surface and the radiation detector device.

2. The apparatus according to claim 1, wherein the radiation scattering device is essentially completely surrounded by a radiation-absorbent region.

3. The apparatus according to claim 1, wherein a second radiation scattering device is provided, and the first and the second radiation scattering device are arranged essentially symmetrically with respect to a centre plane (E) of the apparatus.

4. The apparatus according to claim 1, wherein the first radiation scattering device and the first illumination device are arranged on different sides with respect to a centre plane (E) of the apparatus.

5. The apparatus according to claim 4, wherein two radiation scattering devices are provided which are arranged symmetrically with respect to the centre plane (E) of the apparatus, and also two illumination devices which respectively illuminate the radiation scattering devices located opposite them with respect to the centre plane (E) of the apparatus.

6. The apparatus according claim 1, wherein at least one illumination device is arranged within a radiation scattering device.

7. The apparatus according to claim 1, wherein the apparatus has a housing with an opening, through which the surface can be illuminated.

8. The apparatus according to claim 7, wherein the radiation scattering device is arranged in a side wall of the housing.

9. The apparatus according to claim 1, wherein at least one radiation scattering device is arranged at a distance from the surface in a direction perpendicular to the surface.

10. The apparatus according to claim 1, wherein a radiation scattering body is provided which runs at least in some sections in the centre plane (E) of the apparatus.

11. The apparatus according to claim 1, further comprising at least one radiation-absorbent cover device for covering said radiation scattering device.

12. A method for analyzing surface properties comprising inspecting a surface to be analyzed using the apparatus as claimed in claim 1.

13. A method for analysing surface properties, wherein a surface to be analyzed is indirectly illuminated by a first illumination device and radiation thrown back from the surface is at least partially received by a radiation detector device and a signal is output which is characteristic of the radiation received by the radiation detector device, wherein a radiation scattering device is provided which is at least partially illuminated by the first illumination device and which scatters radiation, and transmits the scattered radiation onto the surface to be analyzed, wherein the radiation scattering device is arranged outside a plane (E) which is arranged through a first radiation direction (R1), in which rays are transmitted from the first radiation device to the surface, and a second radiation direction (R2) which extends between the surface and the radiation detector device.

14. The method according to claim 13, wherein the surface properties are selected from the group consisting of gloss, orange peel, colour, macrostructure, microstructure, image sharpness, haze, surface structure and surface topography.

15. The method according to claim 13, wherein the surface properties are selected from the group consisting of gloss, orange peel, colour, macrostructure, microstructure, image sharpness, haze, surface structure and surface topography.

* * * * *